United States Patent
Lee et al.

(10) Patent No.: US 10,776,666 B2
(45) Date of Patent: Sep. 15, 2020

(54) APPARATUS AND METHOD FOR DIAGNOSIS OF MEDICAL IMAGE

(71) Applicant: SAMSUNG ELECTRONICS CO., LTD., Suwon-si (KR)

(72) Inventors: Ki Yong Lee, Suwon-si (KR); Seung Woo Ryu, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 286 days.

(21) Appl. No.: 14/929,532

(22) Filed: Nov. 2, 2015

(65) Prior Publication Data

US 2016/0171683 A1 Jun. 16, 2016

(30) Foreign Application Priority Data

Dec. 15, 2014 (KR) .......... 10-2014-0180642

(51) Int. Cl.
| | |
|---|---|
| *G06K 9/62* | (2006.01) |
| *G16H 50/70* | (2018.01) |
| *G16H 50/20* | (2018.01) |
| *G06F 19/00* | (2018.01) |

(52) U.S. Cl.
CPC .......... *G06K 9/6262* (2013.01); *G16H 50/20* (2018.01); *G16H 50/70* (2018.01); *G06F 19/321* (2013.01)

(58) Field of Classification Search
CPC .................................................. G06T 7/0012
See application file for complete search history.

(56) References Cited

U.S. PATENT DOCUMENTS

| | | | | |
|---|---|---|---|---|
| 6,553,356 | B1* | 4/2003 | Good | G06F 19/321 |
| | | | | 382/156 |
| 6,983,063 | B1* | 1/2006 | Novak | A61B 6/032 |
| | | | | 382/131 |
| 7,263,214 | B2 | 8/2007 | Uppaluri et al. | |
| 7,367,946 | B2* | 5/2008 | Kato | A61B 8/14 |
| | | | | 382/128 |
| 8,014,576 | B2* | 9/2011 | Collins | A61B 8/08 |
| | | | | 382/128 |
| 8,162,833 | B2 | 4/2012 | Zhang et al. | |
| 8,600,133 | B2* | 12/2013 | Buelow | G06T 7/0012 |
| | | | | 382/128 |
| 2003/0095697 | A1* | 5/2003 | Wood | A61B 6/032 |
| | | | | 382/131 |
| 2005/0102315 | A1* | 5/2005 | Krishnan | G06T 7/0012 |
| 2005/0129297 | A1* | 6/2005 | Kamath | A61B 5/1075 |
| | | | | 382/132 |

(Continued)

FOREIGN PATENT DOCUMENTS

WO 97/09930 A1 3/1997

*Primary Examiner* — Nay A Maung
*Assistant Examiner* — Jose M Torres
(74) *Attorney, Agent, or Firm* — Sughrue Mion, PLLC

(57) ABSTRACT

An apparatus for diagnosis of a medical image includes a storage having a predetermined size, the storage being configured to store sample frames sampled from among received frames which are received from a medical imaging device; a frame collector configured to, once a reference frame is determined, collect one or more sample frames stored in the storage; and a diagnosis component configured to provide a diagnosis for the reference frame based on diagnostic results associated with the one or more collected sample frames.

20 Claims, 10 Drawing Sheets

(56) References Cited

U.S. PATENT DOCUMENTS

| | | | |
|---|---|---|---|
| 2006/0274928 A1* | 12/2006 | Collins | A61B 6/00 382/132 |
| 2007/0053566 A1* | 3/2007 | Kim | G01S 15/8977 382/128 |
| 2009/0143676 A1* | 6/2009 | Matsumura | A61B 8/08 600/438 |
| 2009/0268952 A1* | 10/2009 | Schaffer | G06K 9/6217 382/128 |
| 2009/0292551 A1* | 11/2009 | Sirohey | G06F 19/321 705/2 |
| 2010/0063393 A1* | 3/2010 | Moradi | A61B 8/0833 600/442 |
| 2011/0002515 A1* | 1/2011 | Futami | G06F 19/321 382/128 |
| 2011/0268338 A1 | 11/2011 | Collins et al. | |
| 2012/0157850 A1 | 6/2012 | Sumi et al. | |
| 2013/0018265 A1* | 1/2013 | Kim | A61B 8/145 600/443 |
| 2013/0202173 A1* | 8/2013 | Buckler | G06T 7/0012 382/131 |
| 2013/0310690 A1* | 11/2013 | Chang | A61B 8/08 600/443 |
| 2013/0326386 A1* | 12/2013 | Vendrell | G06F 19/321 715/771 |
| 2014/0194722 A1* | 7/2014 | Lee | A61B 8/085 600/407 |
| 2015/0351725 A1* | 12/2015 | Muramatsu | A61B 8/5246 600/443 |

* cited by examiner

APPARATUS AND METHOD FOR DIAGNOSIS OF MEDICAL IMAGE

CROSS-REFERENCE TO RELATED APPLICATION(S)

This application claims priority from Korean Patent Application No. 10-2014-0180642, filed on Dec. 15, 2014, in the Korean Intellectual Property Office, the entire disclosure of which is incorporated herein by reference for all purposes.

BACKGROUND

1. Field

The following description relaters to an apparatus and method for diagnosis relating to a medical image for enhancement of diagnostic accuracy.

2. Description of the Related Art

Using an ultrasonic medical image diagnostic device, a user is able to monitor a region of interest (ROI) in real time and check various features of a lesion. However, in an existing ultrasonic examination, a user selects only one of several real-time still images output on a screen and can provide diagnoses only about the selected image, so that the diagnostic result may be inaccurate. In addition, since only a single image is considered in the diagnosis, the image that is selected may be a crucial point that affects in a diagnostic result. In addition, making only one or two determinations, such as whether an ROI is malignant or benign, is a relatively easy task that can be performed with high accuracy. However, if there are a number of tasks, it may be hard to achieve highly accurate results using only a single still image. For example, in a case where a user need to check Breast Image Reporting And Data System (BI-RADS) lexicon categories during an ultrasonic examination for breast cancer, if the user manually selects a single still image and diagnoses only the selected image, diagnostic results regarding some BI-RADS lexicon categories may not be accurate enough.

SUMMARY

According to an aspect of an exemplary embodiment, an apparatus for diagnosis of a medical image includes a storage having a predetermined size, the storage being configured to store sample frames sampled from among received frames which are received from a medical imaging device; a frame collector configured to, once a reference frame is determined, collect one or more sample frames stored in the storage; and a diagnosis component configured to provide a diagnosis for the reference frame based on diagnostic results associated with the one or more collected sample frames.

The storage may be configured to sample the received frames according to at least one from among a predetermined selection standard, a variable selection standard for a variable situation, or an empirical selection standard.

The storage may be configured to store sample frames that are selected by an input of a user.

The frame collector may be configured to collect sample frames having a region of interest (ROI) that corresponds to an ROI in the reference frame.

The diagnosis component may include a diagnostic result handler configured to provide diagnostic results associated with the one or more collected sample frames, and to support the diagnosis for the reference frame by combining the diagnostic results associated with the one or more collected sample frames.

The diagnostic result handler may be configured to classify the combined diagnostic results into a plurality of categories and calculate statistical data for each category of the plurality of categories.

The diagnosis component may be configured to assign weights to the diagnostic results according to one or more standards, and provide the diagnosis for the reference frame based on the diagnostic results assigned with the weights.

The apparatus may further include a display component configured to display at least one from among the diagnosis for the reference frame and the diagnostic results associated with the one or more collected sample frames using statistical information relating to frequency distribution.

According to another aspect of an exemplary embodiment, an apparatus for diagnosis of a medical image includes a frame selector configured to sample frames once a reference frame is determined, and select one or more frames to be used for diagnosis of the reference frame; and a diagnosis component configured to provide a diagnosis for the reference frame based on diagnostic results associated with the one or more selected frames.

The frame selector may be configured to sample the frames according to at least one from among a predetermined selection standard, a variable selection standard for a variable situation, an empirical selection standard.

The predetermined selection standard may include at least one from among a predetermined period of time, size of a storage, a total number of frames to be sampled, and accuracy of diagnosis.

The variable selection standard may include comparing at least one from among a change with respect to a probe or a change with respect to a frame.

The empirical selection standard may be based on an indicator associated with learning or inferring an intention of a user.

The frame selector may be configured to select frames having an ROI corresponding to an ROI in the reference frame as selected frames.

The diagnosis component may be configured to generate diagnostic results associated with the selected frames and to support the diagnosis for the reference frame by combining the diagnostic results associated with the selected frames.

The diagnosis component may be configured to classify the combined diagnostic results into a plurality of categories, calculate statistical data for each category of the plurality of categories, and provide the diagnosis for the reference frame using the calculated statistical data.

The diagnosis component may be configured to assign weights to the diagnostic results associated with the selected frames according to one or more standards, and provide the diagnosis for the reference frame based on the diagnostic results assigned with the weights.

According to yet another aspect of an exemplary embodiment, a method for diagnosis of a medical image includes sampling frames from among received frames, the received frames being received from a medical imaging device; storing the sample frames within a storage having a predetermined size; once a reference frame is determined, collecting one or more sample frames to be used for diagnosis of the reference frame; and providing a diagnosis for the reference frame based on diagnostic results associated with the one or more collected sample frames.

The received frames may be sampled according to at least one from among a predetermined selection standard, a variable selection standard for a variable situation, an empirical selection standard.

The providing a diagnosis for the reference frame may include combining the diagnostic results associated with the one or more collected sample frames, and providing the diagnosis for the reference frame using statistical information associated with the combined diagnostic results.

According to a further aspect of an exemplary embodiment, a method of diagnosing a medical image includes sampling frames once a reference frame is determined; selecting one or more frames from among the sample frames; and providing a diagnosis for the reference frame based on diagnostic results associated with the one or more selected sample frames.

According to a still further exemplary embodiment, a method of providing a diagnosis includes storing a plurality of frames received from a medical imaging device; in response to a reference frame being designated, selecting a plurality of selected frames from among the plurality of stored frames; generating a plurality of diagnoses associated with the plurality of selected frames; and generating a diagnosis associated with the reference frame based on the plurality of diagnoses.

Other features and aspects may be apparent from the following detailed description, the drawings, and the claims.

Figure 1A:
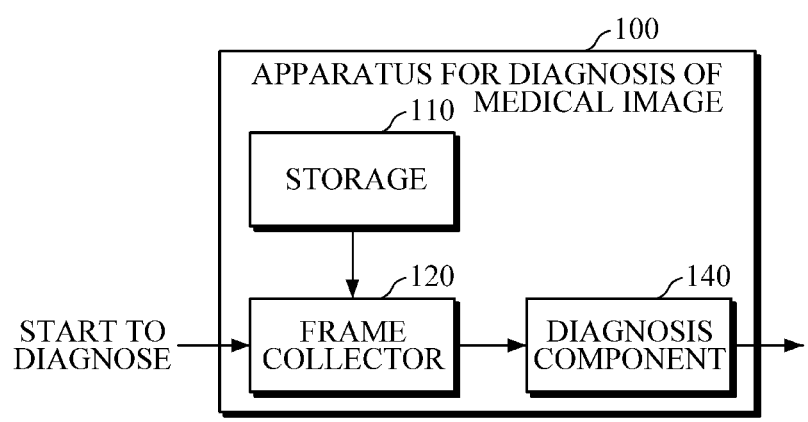
FIG. 1A is a block diagram illustrating an example of an apparatus for diagnosis of a medical image.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

Hereinafter, apparatus and method for diagnosis of a medical image according to exemplary embodiments of the present disclosure are described in detail with reference to drawings.

Figure 1B:
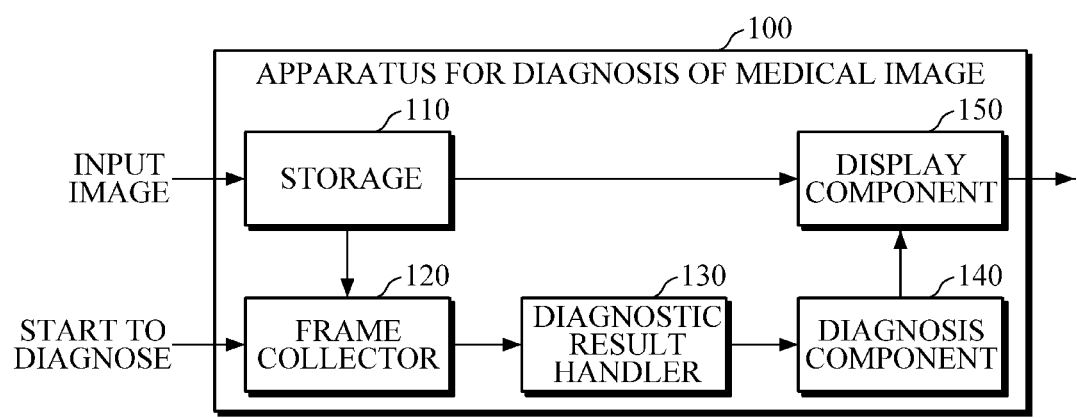
FIG. 1B is a block diagram illustrating a detailed configuration of an apparatus for diagnosis of a medical image.

FIGS. 1A and 1B are block diagrams illustrating an example of an apparatus for diagnosis of a medical image according to an exemplary embodiment. Referring to FIG. 1A, an apparatus 100 for diagnosis of a medical image includes a storage 110, a frame collector 120, and a diagnosis component 140.

The storage 110 samples frames from among frames received from a medical imaging device, and stores the sampled frames in a storage having a predetermined size. For example, in the case of ultrasound examination, a plurality of consecutive frames may be received over time from a probe. If all of the received frames are used for diagnosis of a reference frame, it may cause slow-down of the whole computation. Alternatively, the storage 110 may store some of the received frames at predetermined time intervals by considering limited storage capacity. The storage 110 may function as a buffer or a temporary storage that stores and updates a received frame in real time.

The storage 110 may sample frames among frames received from a medical imaging device according to a predetermined standard, and store the sampled frames. For example, the storage 110 may sample frames according to a predetermined typical selection standard, a variable selection standard for a variable situation, an empirical selection standard, or a combination thereof.

Once a reference frame is determined, the frame collector 120 collects one or more frames to be used for diagnosis of the reference frame from among the stored frames. The reference frame may be determined automatically or in response to an input from a user. Once the reference frame is determined, the frame collector 120 may collect not just the reference frame that is an object to be diagnosed by the diagnosis component 140, but also one or more frames to be used for diagnosis of the reference frame.

The diagnosis component 140 diagnoses the reference frame using a diagnostic result for each collected frame. Diagnosing a frame can, for example, mean providing a diagnosis based on or according to information contained in a frame, or information that is represented by a frame. According to an exemplary embodiment, the diagnosis component 140 may classify a region of interest (ROI) included in the reference frame according to each characteristic, such as shape, orientation, margin, lesion boundary, echo pattern, posterior acoustic features, surrounding tissue, or any other type of characteristic. For the determination, the diagnosis component 140 may use a diagnostic result for each collected frame.

For example, the diagnosis component 140 may combine diagnostic results for all collected frames, classify the combined diagnostic results into categories, calculate statistical data for each category, and use the statistical data for diagnosis of the reference frame. Each diagnostic result for a collected frame may be a classification result regarding an ROI in the frame according to each characteristic, a determination as to whether the ROI in the frame is benign, malignant, negative, or any other determination, based on a probability of the ROI to be a lesion, or a determination as to which subcategories (or subclasses) the ROI in the frame falls within based on a probability of the ROI to be a lesion. In addition, the diagnosis component 140 may diagnose an ROI in a reference frame based on a probability of the ROI to be a lesion.

If diagnostic results for a plurality of frames are used to diagnose a reference frame, it is possible to obtain a more accurate and objective result for the reference frame, compared to when diagnosing only the reference frame. For example, if more frames are collected, more diagnostic results may be classified as primary categories that are considered significant when statistical information is calculated, thereby reducing diagnostic errors. In addition, if diagnostic results for collected frames are classified into categories, such as shape, orientation, margin, lesion boundary, echo pattern, posterior acoustic features, surrounding tissue, and the like, and then used for diagnosis of the reference frame, a more accurate diagnostic result for the reference frame may be obtained, compared to when diagnosing only the reference frame.

Detailed configuration of an exemplary embodiment is provided with reference to FIG. 1B. FIG. 1B is a diagram illustrating an example of detailed configurations of the apparatus shown in FIG. 1.

Referring to FIG. 1B, the apparatus 100 includes the storage 110, the frame collector 120, a diagnostic result handler 130, the diagnosis component 140, and a display component 150.

The storage 110 samples frames among frames received from a medical imaging device, and stores the sampled frames in a storage having a predetermined size. According to an exemplary embodiment, the storage 110 may sample frames according to a predetermined typical selection standard, a variable selection standard for a variable situation, an empirical selection standard, or a combination of any two or more thereof.

The typical selection standard may utilize one or more of the following: a predetermined time interval, size of a storage, the total number of frames to be selected, and accuracy of diagnosis. For example, the storage 110 may sample received frames in predetermined time intervals. In another example, the storage 110 may set a size of a storage and the total number of frames to be sampled in advance, and use this as a frame selection standard. In yet another example, the storage 110 may sample frames by taking into consideration accuracy of diagnosis. If highly accurate diagnosis is required, the storage 110 may set a short sampling interval for a wider area so as to sample more frames. In this case, more sample data may be obtained, thereby improving accuracy of diagnosis of a reference frame.

In addition, the storage 110 may select frames according to a variable selection standard for a variable situation. There may be various selection standards used for sampling frames in a variable situation. The following description is about a selection standard that compares probe variation or frame variation with a threshold level.

According to an exemplary embodiment, when a user conducts an ultrasound examination using a probe of a medical imaging device, the apparatus 100 receives a frame from the probe. Thus, if a position, angle, or speed of the probe is changed, a frame to be received from the probe is thereby changed. In this case, if a degree in change of the position, angle, or speed of the probe is greater than a threshold level, the storage 110 may sample corresponding frames.

According to another exemplary embodiment, the storage 110 may sample a frame if a degree of change in the frame is greater than a threshold level. For example, if a degree of change in a location, size, or shape of a detected ROI in a frame is greater than a threshold level, the storage 110 may sample frames before and after the frame.

In another exemplary embodiment, the storage 110 may sample a frame in a case where difference between the frame and a previous frame is greater than a threshold level. For example, if an ROI in a frame captured at t-n and an ROI a frame captured at t are compared and then difference between the two frames is greater than a threshold level, the storage 110 may sample both of the frames.

According to yet another exemplary embodiment, the storage 110 may further store a frame that is selected in response to an input from a user. For example, in the case of the ultrasound examination, a frame is received in real time, and a user may immediately store a frame required to be further checked, by using a probe, a button, a keyboard, a touch pad, a sensed motion, and the like. The storage 110 may sample a frame that is selected in response to an input from the user.

According to yet another exemplary embodiment, the storage 110 may sample frames according to an empirical selection standard that is based on an indicator learning or inferring intention of a user. For example, a user may take a close look at an ROI and surroundings thereof for a long time. During an ultrasound examination, a user generally diagnoses an ROI by observing frames surrounding the ROI. According to the empirical selection standard, the storage 110 may automatically sample the frame having the ROI that is observed carefully by the user. For example, if frames having the same ROI are received for a predetermined period of time, the storage 110 may automatically sample the received frames.

Once a reference frame is determined, the frame collector 120 collects one or more frames to be used for diagnosis of the reference frame among stored frames. According to an exemplary embodiment, once a reference frame is determined, the frame collector 120 may collect frames having an ROI that corresponds to an ROI included in the reference frame. A determination as to whether an ROI in a specific frame corresponds to an ROI in the reference frame may be made based on similarity there between. For example, if a similarity level between an ROI in a specific frame and an ROI in a reference frame is greater than a threshold level, the ROI in the specific frame may be determined to be the same as an ROI in the reference frame, and then the frame collector 120 may collect frames having the same ROI as that of the reference frame. In addition, in the case where a reference frame includes a plurality of ROIs, the frame collector 120 may collect frames having an ROI to be diagnosed among a plurality of ROIs in the reference frame.

According to another exemplary embodiment, the frame collector 120 may collect frames received before a reference frame among frames that are sampled and stored. For example, the frame collector 120 may collect frames that have been stored a predetermined time before a reference frame.

The apparatus 100 may further include a diagnostic result handler 130 that diagnoses each of the collected frames and handles a process to support diagnosis of the reference frame by combining the diagnostic results for the collected frames. For example, the diagnostic result handler 130 may combine diagnostic results for a plurality of collected frames, classify the combined diagnostic results into categories, and calculate statistical data for each category. A diagnostic result for each collected frame may be a classification result regarding an ROI included in each frame according to each characteristic, a determination as to whether the ROI in the frame is benign, malignant, negative, or other based on a probability of the ROI to be a lesion, or a determination as to which subcategories (or subclasses) the ROI in the frame falls within based on a probability of the ROI to be a lesion.

The subcategories may be Breast Imaging-Reporting And Data System (BI-RADS) categories. BI-RADS was initially used for X-ray mammogram of breasts, and now is widely used for MRI and ultrasonic medical imaging devices. The BI-RADS categories consist of incomplete(0), Negative(1), Benign finding(2), Probably benign finding(3), Suspicious abnormality(4), Highly suggestive of malignancy(5), and Known biopsy-proven malignancy(6). However, the above are merely exemplary, and a different number of categories with different names may be contemplated as falling within the scope of the exemplary embodiments.

The diagnostic result handler 130 may combine diagnostic results for any number, for example hundreds, of collected frames having the same ROI, classify the combined diagnostic results into categories, and calculate statistical data for each category. The diagnostic result handler 130 may determine a primary category to which the largest number of the diagnostic results belong. Hundreds of frames are merely exemplary, and aspects of the present disclosure are not limited thereto.

The diagnosis component 140 performs diagnosis on a reference frame using a diagnostic result for each collected frame. According to an exemplary embodiment, the diagnosis component 140 may classify an ROI in the reference frame according to each characteristic, such as shape, orientation, margin, lesion boundary, echo pattern, posterior acoustic features, surrounding tissue, or any other type of characteristic. The diagnosis component 140 may use a diagnostic result for each collected frame. For example, in the case where the diagnosis component 140 analyzes a shape of the ROI in the reference frame, the diagnosis component 140 may combine diagnostic results on shape of a plurality of collected frames, and classify a shape of the ROI in the reference frame using the statistical information on the shape. Detailed descriptions of the above process are provided with reference to FIG. 6A.

According to another exemplary embodiment, the diagnosis component 140 may diagnose an ROI in a reference frame to see whether the ROI is benign, malignant, negative, or other based on a probability of the ROI to be a lesion thereof or which subcategories the ROI falls within. In this case, the diagnosis component 140 may combine diagnostic results for ROIs in a plurality of collected frames, and diagnose the ROI in the reference frame using statistical information regarding the combined diagnostic results.

According to another exemplary embodiment, the diagnosis component 140 may assign weights to diagnostic results for collected frames according to one or more standards, and diagnose a reference frame based on the diagnostic results assigned with the weights. For example, the diagnosis component 140 may diagnose the reference frame by assigning a weight to a category to which the largest number of diagnostic results belong. There may be various methods of assigning a weight, and it is possible to assign a weight to each characteristic or each category. In addition, the diagnosis component 140 may assign a weight to a frame collected at a point in time close to the time of determination of the reference frame to be diagnosed. Further, a lesion's feature, confidence, accuracy, and any other additional factors may be considered. There may be various standards for assigning a weight, so any other examples may be contemplated as falling within the scope of the exemplary embodiments.

The display component 150 displays diagnostic results for one or more frames. According to an exemplary embodiment, the display component 150 may display a diagnostic result on whether an ROI in a reference frame is negative, benign, malignant, or other. According to another exemplary embodiment, using statistical information that represents frequency distribution characteristics of a combined diagnostic results for collected frames, the display component 150 may display a diagnostic result for an ROI in a reference frame. For example, the display component 150 may display a histogram that indicates statistical information on diagnostic results for a plurality of collected frames, and display a diagnostic result for the reference frame above the histogram. In addition, other various types of statistic information, including a pie chart, a bar graph, and a graph of broken line, may be used. If a number of frames are collected, it may be visually more effective to display statistical information that represents diagnostic results accumulated for each category. In addition, if there are two or more reference frames, the display component 150 may visually display statistical information regarding diagnostic results for the reference frames.

Figure 2:
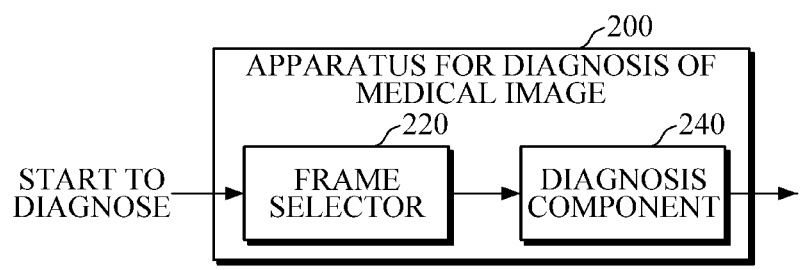
FIG. 2 is a block diagram illustrating another example of an apparatus for diagnosis of a medical image.

FIG. 2 is a block diagram illustrating an apparatus for diagnosis of a medical image according to another exemplary embodiment. Referring to FIG. 2, an apparatus 200 for diagnosis of a medical image includes a frame selector 220 and a diagnosis component 240.

Once a reference frame is determined, the frame selector 220 samples frames and selects one or more sampled frames to be used for diagnosis of the reference frame. The frame selector 220 may sample frames received from a medical imaging device, select frames to be used for diagnosis of the reference frame, and store the selected frames.

In addition, the frames received from the medical imaging device and the frames selected by the frame selector 220 may be stored in a storage. The storage may be an important or integral element, and it does not matter when the frames are stored. For example, the frames may be sampled and stored simultaneously or sequentially.

The reference frame may be determined automatically or in response to an input from a user. If a diagnosis initiating command or request is received, the apparatus 200 may automatically determine a reference frame to be diagnosed. In other exemplary embodiments, if a user explicitly selects a frame, for example, by pressing a button or inputting a key using a probe during the examination, the apparatus 200 may consider the selection a diagnosis initiating command or request, and determine that the selected frame is a reference frame to be diagnosed.

Once the reference frame is determined, the frame selector 220 may perform sampling according to a predetermined standard. For example, the frame selector 220 may sample frames using a predetermined typical selection standard, a variable selection standard for a variable situation, an empirical selection standard, or a combination of any two or more thereof.

The typical selection standard may utilize at least one of the following: a predetermined period of time, size of a storage, the total number of frames to be selected, and accuracy of diagnosis. For example, the frame selector 220 may periodically sample frames that are received at predetermined time intervals. In another example, the frame selector 220 may set in advance size of a storage and the total number of frames to be sampled, and use the same when selecting frames. In yet another example, the frame selector 220 may sample frames by taking into consideration diagnosis accuracy. If highly accurate diagnosis is required, the frame selector 220 may set a short sampling interval for a wider area so as to sample more frames. In this case, more sample data may be obtained, thereby improving accuracy in diagnosis of a reference frame.

In addition, the frame selector 220 may select frames by a variable selection standard for a variable situation. There may be various variable selection standards for a variable situation. Hereinafter, there is described a selection standard in which change with respect to a probe or a frame is compared with a threshold level.

According to an exemplary embodiment, if a position, angle, or speed of a probe is changed, a frame to be received from the probe may be thereby changed. In this case, in a case where a degree of change in a position, angle, or speed of the probe is greater than a threshold level, the frame selector 220 may sample a frame.

In another exemplary embodiment, a degree of change in each characteristic of a frame may be compared. In the case where a degree of change in each characteristic, such as shape, orientation, margin, lesion boundary, echo pattern, posterior acoustic features, surrounding tissue, or any other characteristic, of a frame is greater than a threshold level, the frame selector 220 may sample the frame. For example, in the case where a degree of change in location, size, or shape of a detected ROI in a frame is greater than a threshold level, the frame selector 220 may sample frames before and after the frame.

In another exemplary embodiment, in the case where difference between a specific frame and a previous frame is greater than a threshold level, the frame selector 220 may sample both of the frames. For example, the frame selector 220 may compare an ROI in a frame captured at t-1 with an ROI in a frame captured at t, and, if difference between the two frames is greater than a threshold level, the frame selector 220 may sample both of the frame at t-1 and the frame at t.

According to yet another exemplary embodiment, the frame selector 220 may further store frames that are explicitly selected in response to a user's input. For example, frames are received in real time in the case of an ultrasound examination, so a user may immediately store any frame necessary to be further checked, by using a probe, a button, a keyboard, a touch pad, a sensed motion, and the like. The frame selector 220 may sample frames that are explicitly selected in response to an input from the user.

In addition, the frame selector 220 may sample frames using an empirical selection standard that is based on an indicator learning or inferring intention of a user. According to an exemplary embodiment, the user may take a close look at an ROI, for example, by observing an area surrounding the ROI for a long time. When conducting an ultrasound examination, a user diagnoses an ROI by observing frames surrounding the ROI. According to the empirical selection standard, the frame selector 220 may automatically sample frames having an ROI that is carefully observed by a user. For example, if frames having the same ROI are received for a predetermined period of time, the frame selector 220 may automatically sample the received frames.

During or after the sampling, the frame selector 220 may select frames having an ROI which corresponds to an ROI included in a reference frame, wherein the selected frames are to be used for diagnosis of the reference frame. In a case where a reference frame includes a plurality of ROIs, the frame selector 220 may select a frame having any ROI that is subject to be diagnosed among a plurality of ROIs in the reference frame. Whether an ROI in a specific frame corresponds to an ROI in the reference frame may be determined based on similarity between the ROIs. For example, if a similarity level between an ROI in a specific frame and an ROI in a reference frame is greater than a threshold level, the ROI in the specific frame may be determined to be the same as that of the reference frame. Based on the determination, the frame selector 220 may collect frames having the same ROI as that of the reference frame. In addition, in a case where a reference frame includes a plurality of ROIs, the frame selector 220 may collect frames having an ROI to be diagnosed among a plurality of ROIs in the reference frame.

The diagnosis component 240 diagnoses on the reference frame based on diagnostic results for the selected frames. According to an exemplary embodiment, based on diagnostic results for the selected frames, the diagnosis component 240 may classify an ROI in the reference frame according to each characteristic, such as shape, orientation, margin, lesion boundary, echo pattern, posterior acoustic features, surrounding tissue, or the like. In addition, the diagnosis component 240 may diagnose an ROI in the reference frame based on a probability of the ROI in the reference frame to be a lesion.

For example, the diagnosis component 240 may combine diagnostic results for any number, for example hundreds of frames having the same ROI, classify the combined diagnostic results into categories, calculate statistical data for each category, and use the calculated statistical information. Each diagnostic result for a selected frame may be a classification result regarding an ROI in the frame according to each characteristic, a determination as to whether the ROI in the frame is benign, malignant, negative or other, or a determination as to whether the ROI in the frame falls within which subcategories based on a probability of the ROI to be a lesion.

According to yet another exemplary embodiment, the diagnosis component 240 may assign weights to diagnostic results for collected frames according to one or more standards, and diagnose a reference frame based on the diagnostic results assigned with the weights. For example, the diagnosis component 240 may assign a weight to a category to which the largest number of diagnostic results belong, and diagnose a reference frame based on the diagnostic results assigned with the weights. In another example, the diagnosis component 240 may assign a weight to a category with a frequency greater than a predetermined value. There may be various method for assigning a weight, and it is possible to assign a weight to each characteristic or each category. In addition, the diagnosis component 240 may assign a weight to an image that is selected at a time close to the time of determining a reference frame to be diagnosed. In some exemplary embodiments, a lesion's feature, confidence, accuracy, or any other factor may be considered. There may be various standards for assigning a weight, and they should be contemplated as falling within the scope of the exemplary embodiments.

If diagnostic results for a plurality of selected frames are used for diagnosis of a reference frame, it may be possible to obtain a more accurate and objective diagnostic result for the reference frame, compared to diagnosing only the reference frame. For example, if more frames are selected, more diagnostic results to be classified as a category, which is considered significant when statistical information is calculated, may be obtained, thereby possibly reducing diagnostic errors.

In addition, if the diagnostic results for selected frames are classified by characteristics, such as shape, orientation, margin, lesion boundary, echo pattern, posterior acoustic features, surrounding tissue, or any other type of characteristic, and then used for diagnosis of the reference frame, a more accurate diagnostic result may be obtained, compared to diagnosing only the reference frame.

Figure 3:
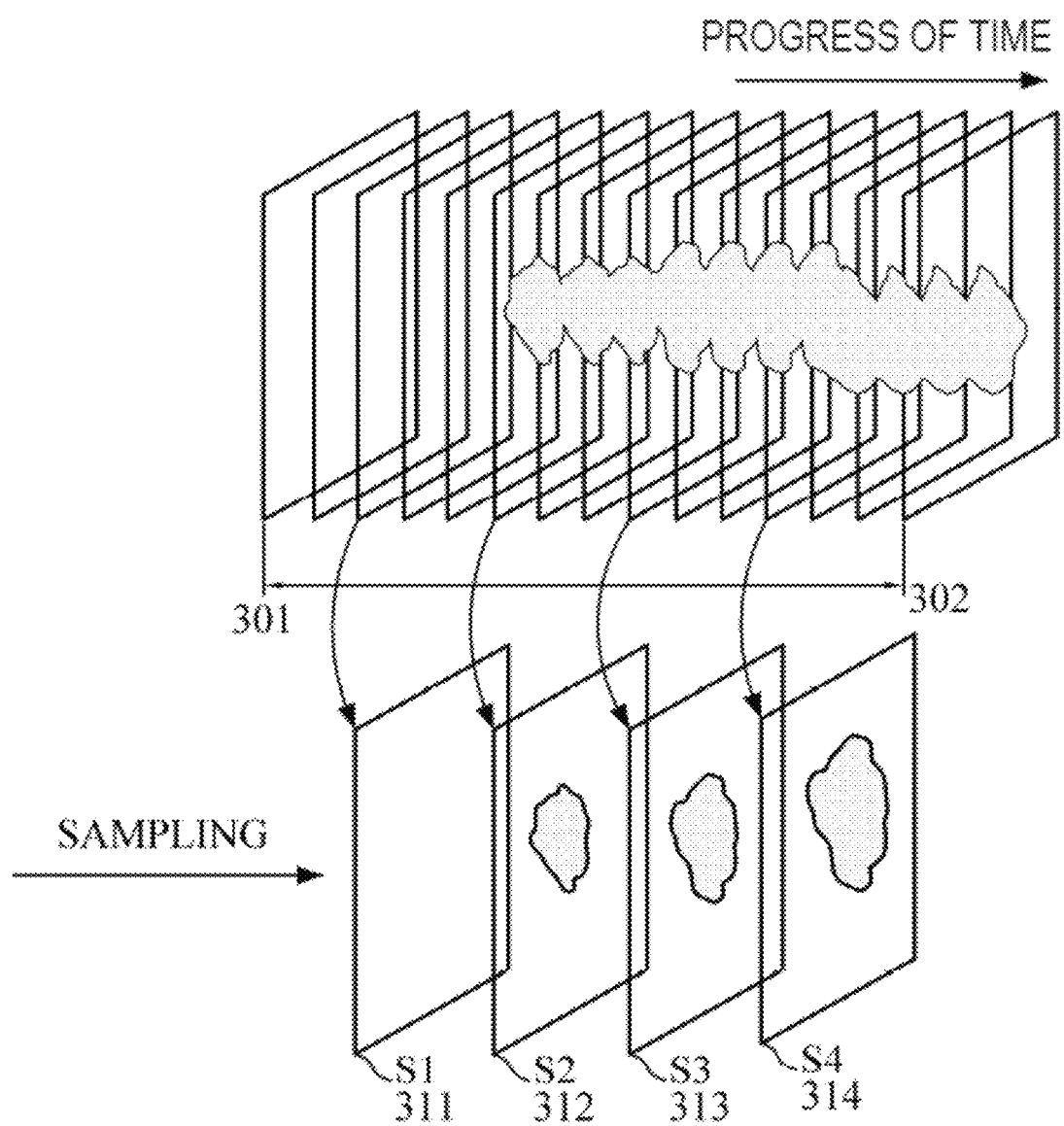
FIG. 3 is a diagram illustrating an example in which an apparatus for diagnosis of a medical image samples frames in predetermined time intervals.
Figure 4:
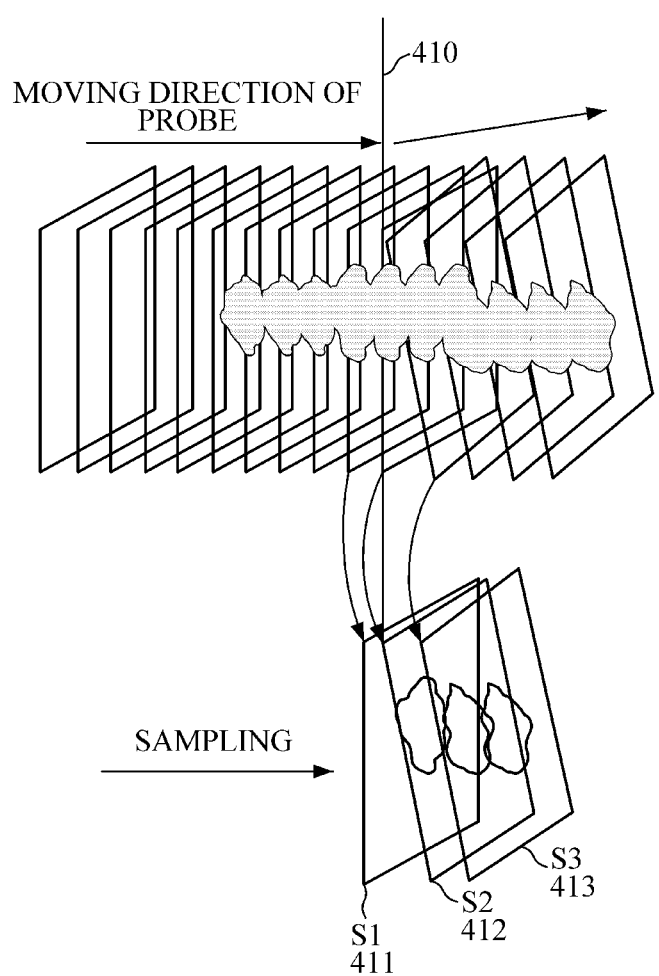
FIG. 4 is a diagram illustrating an example in which an apparatus for diagnosis of a medical image samples frames based on change with respect to a probe.
Figure 5:
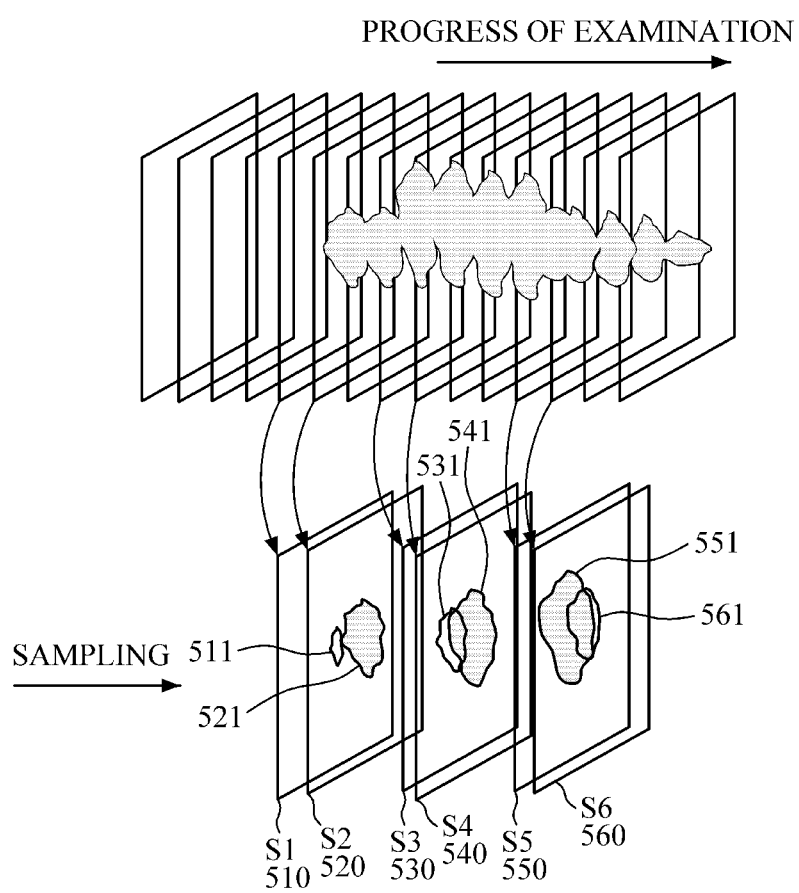
FIG. 5 is a diagram illustrating an example in which an apparatus for diagnosis of a medical image performs sampling based on difference between one frame and a previous frame.

FIGS. 3, 4, and 5 are examples of performing sampling by a specific selection standard. However, there may be various selection standards for sampling a frame, so the examples are not necessarily limited to the following description.

FIG. 3 shows an example in which an apparatus for diagnosis of a medical image samples frames at predetermined time intervals. Referring to FIG. 3, an apparatus for diagnosis of a medical image may perform sampling at predetermined time intervals for the entire frame period (301~302). For example, in a case where a period of time for receiving three frames is set as a time interval, one of the three frames may be sampled. In FIG. 3, an ROI is not detected from a sampled frame S1 311, but detected from a sampled frame S2 312, a sample frame S3 313, and a sampled frame S4 314. In addition, size of the ROI increases over time.

FIG. 4 is a diagram illustrating an example in which an apparatus for diagnosis of a medical image performs sampling based on change with respect to a probe. According to an exemplary embodiment, if location, angle, or speed of a probe is changed, a cross-section orientation of a frame received from the probe is changed, shape, angle, and orientation of an ROI included in the frame is changed. In this case, if frames are collected according to a selection standard that is based on the change with respect to the probe, the apparatus may sample various frames having an ROI with different shape, angle, and orientation.

Referring to FIG. 4, a moving direction of a probe is changed with reference to an axis 410. The change with respect to the probe may be physically measured using a sensor attached to the probe or may be indirectly measured based on an input indicating the variation of the probe. If the change with respect to the probe is greater than a threshold level, an apparatus for diagnosis of a medical image may sample frames received before and after the axis 410. Referring to FIG. 4, if a frame S2 412 is a frame received when a moving direction of a probe is changed, the apparatus may sample a previous frame S1 411 and a subsequent frame S3 413.

FIG. 5 is a diagram illustrating an example in which an apparatus for diagnosis of a medical image performs sampling based on difference between one frame and a previous frame. According to an exemplary embodiment, the apparatus 100 may sample frames that have an amount of changes over a threshold by comparing one frame with a previous frame. Referring to FIG. 5, a frame S1 510 is received when an ROI starts to be detected, and then a frame S2 520 is received. An ROI 521 in the frame S2 520 is bigger than an ROI 511 in the frame S1 510, and there is a big difference in shape between the ROI 511 and the ROI 521. In this case, the apparatus 100 may compare one frame with a previous frame, and, if difference therebetween is greater than a threshold level, sample the one frame. In addition, referring to FIG. 5, an ROI 531 in a frame S3 530 is bigger than an ROI 541 in a frame S4 540, and an ROI 551 in a frame S5 550 is smaller than an ROI 561 in a frame S6 560. In this case, if difference between one frame and the previous frame is greater than a threshold level, the apparatus 100 may sample the one frame.

Figure 6A:
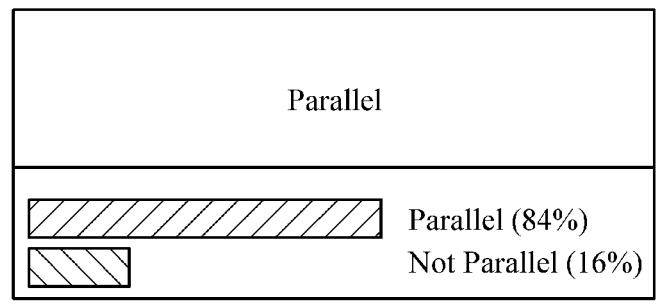
FIG. 6A is a diagram illustrating an example in which an orientation of a reference frame is diagnosed using a diagnostic result for a collected frame.

FIG. 6A is a diagram illustrating an example of determining orientation of a reference frame based on diagnostic results for collected frames. FIG. 6A is described with reference to FIG. 1. When determining some characteristics, such as shape, orientation, margin, lesion boundary, echo pattern, posterior acoustic features, surrounding tissue, or any other desired characteristic, of a reference frame, the apparatus 100 for diagnosis of a medical image may use diagnostic results for collected frames. Referring to FIG. 6A, if one hundred frames are collected, orientation of each frame may be determined. Orientation of each frame is determined based on whether a long axis of an ROI is in parallel to the skin line. If a long axis of an ROI is wider than tall or horizontal, orientation of a corresponding frame is determined to be parallel. Alternatively, if a long axis of an ROI is taller than wide or vertical or includes round, orientation of a corresponding frame is determined to be not parallel.

Referring to FIG. 6A, diagnostic results for collected frames shows that about 84% of the frames is determined to have parallel orientation and about 16% is determined to have non-parallel orientation. The apparatus 100 may combine the collected frames' diagnostic results on orientation, and classify orientation of a reference frame as parallel, based on the combined diagnostic results.

For example, although orientation of a reference frame is classified as not parallel, the apparatus 100 may classify orientation of an ROI in the reference frame as parallel based on diagnostic result for collected frames. In this case, if more frames are collected, more objective statistical information may be applied to diagnose the reference frame.

Figure 6B:
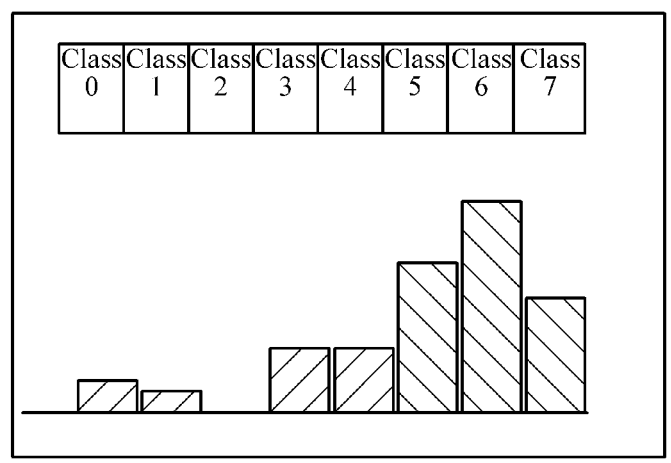
FIG. 6B is a diagram illustrating an example in which a reference frame is diagnosed using a diagnostic result for a collected frame.

FIG. 6B is a diagram illustrating an example of diagnosing an ROI based on diagnostic results for collected frames. Referring to FIG. 6B, the apparatus 100 may classify diagnostic results for collected frames into categories, and display the classification result in a form of histogram. According to an exemplary embodiment, in the case of an ultrasound examination of breast cancer, BI-RADs categories may be used. For example, classes 0 to 6 may consist of_incomplete(0), Negative(1), Benign finding(2), Probably benign finding(3), Suspicious abnormality(4), Highly suggestive of malignancy(5), Known biopsy-proven malignancy(6), respectively. However, name of each class of a classifying standard may differ, so aspects of the present disclosure are not limited thereto. Further, the apparatus 100 may be used in ultrasound examinations for abdomen, thyroid gland, blood vessels, musculoskeletal disorder, and the like, and may be used in any other examination that requires collecting a plurality of medical images.

The apparatus 100 may classify the diagnostic results for the collected frames into categories based on a probability of an ROI in each frame to be a lesion. Then, the apparatus 100 may combine diagnostic results for all the collected frames and display the combined diagnostic results in a form of histogram.

Referring FIG. 6B, a relatively large number of diagnostic results are classified as class 5 to class 7, and the largest number of diagnostic results are classified as class 6. The apparatus 100 may determine primary categories using statistical information regarding the combined diagnostic results. Then, the apparatus 100 may diagnose a reference frame to determine whether the reference frame falls within class 5 (suspicious abnormality), class 6 (known biopsy-proven malignancy), or class 7 (highly suggestive of malignancy).

Figure 7:
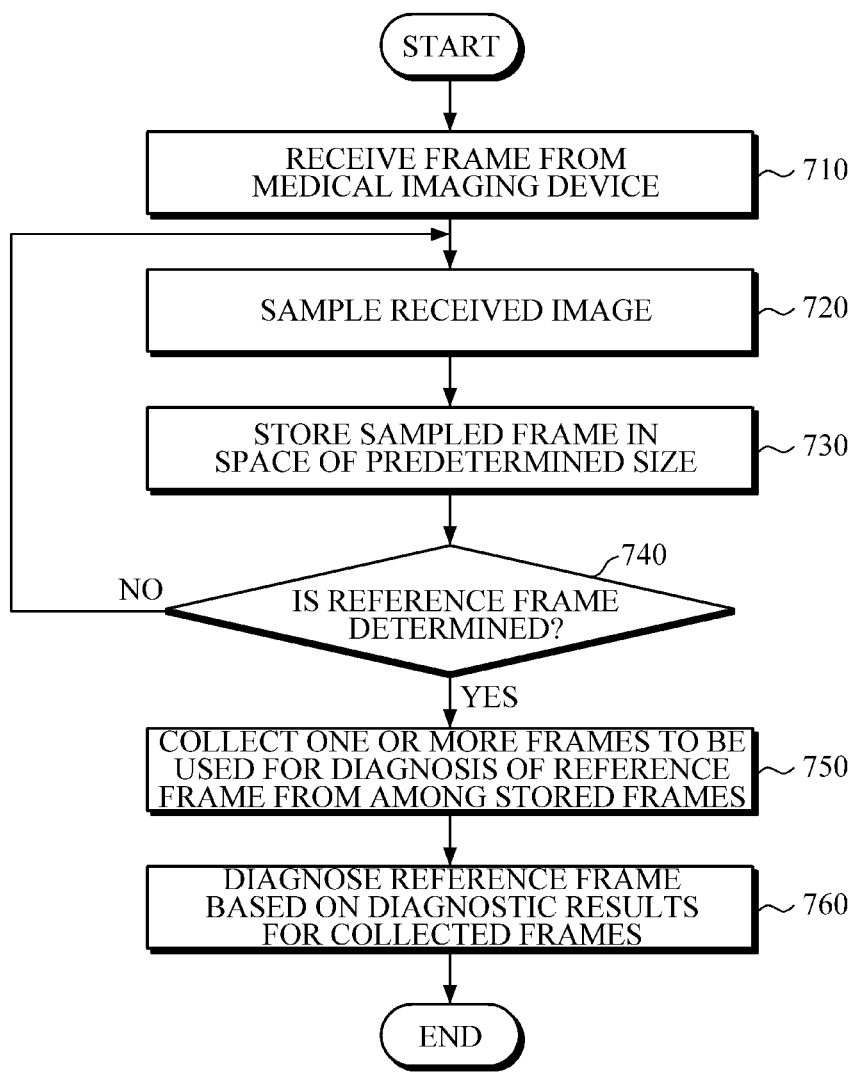
FIG. 7 is a flowchart illustrating a method for diagnosis of a medical image, the method which is implemented by the apparatus shown in FIGS. 1A and 1B.

FIG. 7 is a flowchart illustrating an exemplary method for diagnosis of a medical image, the method that is implemented by the apparatus shown in FIG. 1, according to an exemplary embodiment.

First, the apparatus 100 receives a frame from a medical imaging device in 710. The apparatus 100 samples the received frame in 720, and stores one or more sampled frames in a space of predetermined size in 730. According to an exemplary embodiment, the apparatus 100 may sample frames among frames received from a medical imaging device according to a predetermined standard, and store the sampled frames. For example, the apparatus 100 may sample a frame according to a predetermined typical selection standard, a variable selection standard for a variable situation, an empirical selection standard, or a combination thereof, and store the sampled frame.

The typical selection standard may include one or more of a predetermined period of time, size of a storage, the total number of frames to be selected, and accuracy of diagnosis. For example, the apparatus 100 may periodically sample frames among all frames received for a predetermined period of time. In another example, the apparatus 100 may set size of a storage and the total number of frames to be sampled in advance, and use this as a standard for selecting frames. In yet another example, the apparatus 100 may sample frames by taking into consideration diagnosis accuracy. If highly accurate diagnosis is required, the storage 110 may set a short sampling interval for a wider area so as to sample more frames. In this case, more sample data may be obtained, thereby improving accuracy in diagnosis of a reference frame.

In addition, the apparatus 100 may select a frame according to a variable selection standard for a variable situation. For example, if a position, angle, or speed of a probe is changed, a frame to be received from the probe is thereby changed. Accordingly, when a degree of change in a position, angle, or speed of the probe is greater than a threshold level, the apparatus 100 may sample a frame.

According to another exemplary embodiment, in the case where change with respect to a frame is greater than a threshold level, the apparatus 100 may sample the frame. The change with respect to a frame may include various exemplary embodiments. For example, in the case where a degree of change in location, size, or shape of a detected ROI in a frame is greater than a threshold level, the apparatus 100 may sample frames before and after the frame. In another example, in the case where change with respect to a frame is greater than a threshold level, the apparatus 100 may sample the frame. That is, in the case where difference between on an ROI in a frame at t-1 and an ROI in a frame at t is greater than a threshold level, the apparatus 100 may sample both of the frames.

In another exemplary embodiment, the apparatus 100 may further store frames that are explicitly selected in response to a user's input. For example, in the case of an ultrasound examination, a frame is received in real time, so a user may be able to store any frame necessary to be further checked, by using a probe, a button, a keyboard, a touch pad, a sensed motion, and the like. In this case, the apparatus 100 may sample frames selected in response to the user's input.

According to yet another exemplary embodiment, the apparatus 100 may perform sampling according to an empirical selection standard that is based on an indicator learning or inferring intention of a user. For example, a user may take a close look at an ROI, for example, by observing an area surrounding the ROI for long time. In the case of an ultrasound examination, a user usually diagnoses an ROI by observing frames surrounding the ROI. According to the empirical selection standard, the apparatus 100 may automatically sample a frame having an ROI that is carefully observed by a user. For example, if frames having the same ROI are received for a predetermined period of time, the frame selector 220 may automatically sample the received frames.

Then, the apparatus 100 determines whether a reference frame is determined in 740. If a reference frame to be diagnosed is determined automatically or in response to an input from a user, the apparatus 100 collects, among the stored frames, frames to be used for diagnosis of the reference frame in 750.

According to an exemplary embodiment, if the reference frame is determined, the apparatus 100 may collect frames having an ROI corresponding to an ROI in the reference frame. Whether an ROI corresponds to the ROI included in the reference frame may be determined based on similarity therebetween. For example, if a similarity level between an ROI in a specific frame and an ROI in a reference frame is greater than a threshold level, the ROI in the specific frame may be determined to be same as the ROI in the reference frame, and thus, the apparatus 100 may collect frames having the same ROI as that of the reference frame. In addition, if a reference frame includes a plurality of ROIs, the apparatus 100 may select a frame having a ROI to be diagnosed among a plurality of ROIs in the reference frame.

According to another exemplary embodiment, the apparatus 100 may collect frames that have been stored before a reference frame from among sampled and stored frames. For example, the apparatus 100 may collect frames that were stored before a predetermined period of time has lapsed from a reference frame.

Then, the apparatus 100 may combine diagnostic results for all the collected frames and process the combined diagnostic results. For example, the apparatus 100 may combine diagnostic results for a plurality of frames, classify the combined diagnostic results into categories, and calculate statistical data for each category. A diagnostic result for each collected frame may be a classification result regarding an ROI in the frame according to each characteristic, a determination as to whether the ROI in the frame is benign, malignant, negative, or other based on a probability of the ROI to be a lesion, or whether the ROI falls within which subcategories (or subclasses) based on a probability of the ROI to be a lesion. In addition, the subdivided categories may be BI-RADS categories.

The apparatus 100 may combine diagnostic results for any number, for example hundreds of frames having the same ROI, classify the combined diagnostic results into categories, and calculate statistical data for each category. The apparatus 100 may determine a primary category to which most of the diagnostic results belong. Hundreds of frames are merely exemplary and not necessarily understood as a limited element.

The apparatus 100 diagnoses the reference frame based on diagnostic results for all the collected frames in 760. According to an exemplary embodiment, the apparatus 100 determines shape, orientation, margin, lesion boundary, echo pattern, posterior acoustic features, surrounding tissue, or any other characteristic of an ROI in the reference frame. In this case, the apparatus 100 may use diagnostic results for all the collected frames. For example, in order to determine shape of the ROI in the reference frame, the apparatus 100 may combine diagnostic results on shape of a plurality of collected frames and then classify the ROI in the reference frame based on statistical information regarding the combined diagnostic results.

According to another exemplary embodiment, the apparatus 100 may diagnose an ROI in a reference frame to see whether the ROI is benign, malignant, negative, or other, or falls within which subcategories based on a probability of the ROI to be a lesion. In this case, the apparatus 100 may combine diagnostic results for a plurality of collected frames, and classify the ROI in the reference frame based on statistical information regarding the combined diagnostic results.

According to yet another exemplary embodiment, the apparatus 100 may assign weights to diagnostic results for collected frames according to one or more standards, and diagnose a reference frame based on the diagnostic results assigned with the weights. For example, the apparatus 100 may assign a weight to a category to which the largest number of diagnostic results belong, and diagnose a reference frame based on the diagnostic results assigned with the weights. There may be various methods for assigning a weight, and a weight may be assigned to each characteristic or each category. In addition, the apparatus 100 may assign a weight to an image that is collected at a point in time close to the time of determining a reference frame. Further, a lesion's features, confidence, accuracy, or any other factor may be considered. There may be various methods for assigning a weight, and they may be contemplated as falling within the scope of the exemplary embodiments.

Then, the apparatus 100 may display diagnostic results for one or more frames. For example, the apparatus 100 may display a diagnostic result on whether an ROI in a reference frame is negative, benign, malignant, or other. In addition, the apparatus 100 may display a diagnostic result for the reference frame based on statistical information that presents frequency distribution characteristics of combined diagnostic results for collected frames. For example, the apparatus 100 may display a histogram that indicates statistical information regarding diagnostic results for a plurality of collected frames, and display a classification result of a reference frame above the histogram. Instead of the histogram, the apparatus 100 may use any other statistic information, such as a pie chart, a bar graph, linearized curves, and the like. If more frames are collected, it may be visibly more effective to display a histogram that indicates statistical information on diagnostic results accumulated for each characteristic. In addition, if there are a plurality of reference frames, the apparatus 100 may display statistic information on diagnostic results for the reference frames.

Figure 8:
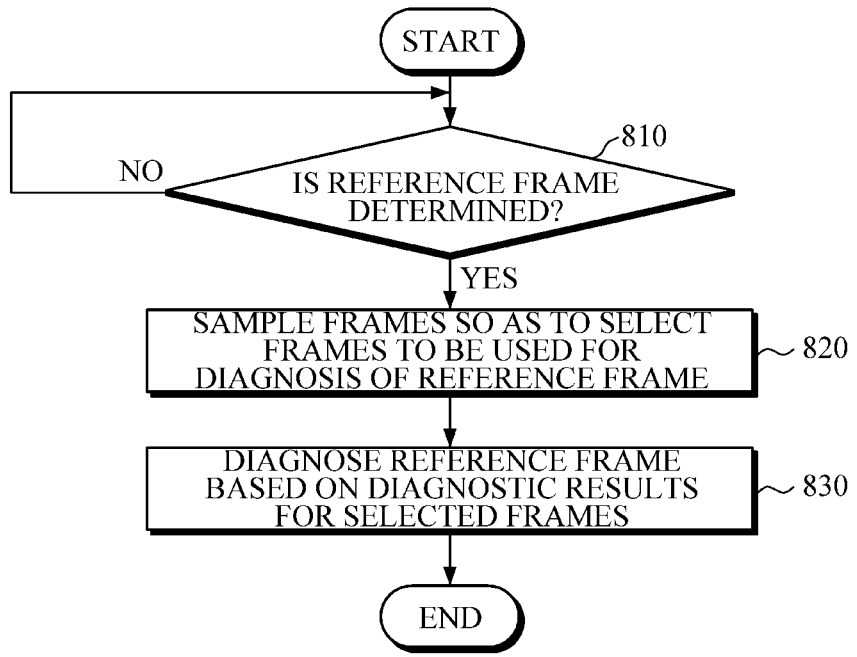
FIG. 8 is a flowchart illustrating a method for diagnosis of a medical image, the method which is implemented by the apparatus shown in FIG. 2.

FIG. 8 is a flowchart illustrating an exemplary method for diagnosis of a medical image, the method which is implemented by the apparatus shown in FIG. 2, according to another exemplary embodiment.

In 810, the apparatus 200 determines whether a reference frame to be diagnosed is determined. The reference frame may be determined automatically or in response to an input from a user. If a command or request for initiating diagnosis is received, the apparatus 200 may automatically determine a reference frame to be diagnosed. Alternatively, if a user explicitly selects a frame by using a button or key of a probe, the apparatus 200 may consider the input a command or request for initiating diagnosis, and determine a reference frame to be diagnosed.

After the reference frame is determined, the apparatus 200 may perform sampling according to a predetermined standard in 820. For example, the apparatus 200 may perform sampling according to a predetermined typical selection standard, a variable selection standard for a variable situation, an empirical selection standard, or a combination thereof.

The typical selection standard may include one or more of a specific period of time, size of a storage, the total number of frames to be selected, and accuracy of a diagnosis result. For example, the apparatus 200 may periodically sample frames received at predetermined time intervals. In another example, the apparatus 200 may set in advance size of a storage and the total number of frames to be sampled, and use the both as a frame selection standard. In yet another example, the apparatus 200 may sample a frame by taking into consideration diagnosis accuracy. If highly accurate diagnosis is required, the apparatus 200 may set a short sampling interval for a wider area so as to sample more frames. In this case, more sample data may be obtained, thereby improving accuracy in diagnosing a reference frame.

In addition, the apparatus 200 may select a frame according to a variable selection standard for a variable situation. There may be various selection standards used for sampling a frame in the variable situation. Hereinafter, there is described a selection standard in which change with respect to a probe or a frame is compared with a threshold level.

According to an exemplary embodiment, if change with respect to a frame is greater than a threshold level, the apparatus 200 may sample the frame. For example, in a case where a degree of change in a position, angle, or speed of a probe is greater than a threshold level, the apparatus 200 may sample a frame.

According to another exemplary embodiment, change in each characteristic of a frame may be compared with a threshold level. Specifically, in the case where a degree of change in each characteristic, such as shape, orientation, margin, lesion boundary, echo pattern, posterior acoustic features, surrounding tissue, or the like, of an ROI in a frame is greater than a threshold level, the apparatus 200 may sample the frame. For example, in the case where a degree of change in a location, size, or shape of an ROI in a frame is greater than a threshold level, the apparatus 200 may sample frames before and after the frame.

According to another exemplary embodiment, the apparatus 200 may perform sampling based on difference between one frame and a previous frame. For example, if difference between an ROI in a frame at t-1 and an ROI in a frame at t is greater than a threshold level, the apparatus 200 may sample both of the frames.

According to yet another exemplary embodiment, the apparatus 200 may further store frames that are selected in response to a user's input. For example, a frame is received in real time in the case of an ultrasound examination, so a user may store a frame necessary to be check later, by using a probe, a button, a keyboard, a touch pad, a sensed motion, and the like. In this case, the apparatus 200 may sample a frame that is selected in response to a user's input.

In addition, the apparatus 200 may perform sampling according to an empirical selection standard that is based on an indicator learning or inferring intention of a user. According to an exemplary embodiment, a user may take a close look an ROI, for example, by observing the ROI for long time. For an ultrasound examination, a user diagnoses an ROI by observing frames surrounding the ROI. According to the empirical selection standard, the apparatus 200 may automatically sample a frame having the ROI that is carefully observed by the user. For example, if frames having the same ROI are received for a specific period of time, the apparatus 200 may automatically sample the received frames.

During or after the sampling process, the apparatus 200 may select a frame having an ROI that corresponds to an ROI in a reference frame and use the selected frame for diagnosis of the reference frame. In a case where in a reference frame includes a plurality of ROIs, the apparatus 200 may select a frame having an ROI subject to be diagnosed among a plurality of ROIs in the reference frame. Whether an ROI in a specific frame corresponds to an ROI in a reference frame may be determined based on similarity there between. For example, in the case where a similarity level between an ROI in a specific frame and an ROI in a reference frame is greater than a threshold level, the ROI in the specific frame may be determined to be the same as the ROI in the reference frame. Then, frames having the same ROI as that of the reference frame may be collected and used for diagnosis of the reference frame.

The apparatus 200 diagnoses the reference frame based on diagnostic results for selected frames in 830. According to an exemplary embodiment, the apparatus 200 may classify an ROI in a reference frame according to each characteristic, such as shape, orientation, margin, lesion boundary, echo pattern, posterior acoustic features, surrounding tissue, or the like. For the classification, the apparatus 200 may use diagnostic results for selected frames. In addition, the apparatus 200 may diagnose an ROI in a reference frame based on a probability of the ROI to be a lesion.

For example, the apparatus 200 may combine diagnostic results for any number, for example hundreds of frames collected for a single ROI, classify the combined diagnostic results into categories, calculate statistical data for each category, and use the calculated statistical data. A diagnostic result for a selected frame may be a classification result regarding an ROI in the frame according to each characteristic, a determination as to whether the ROI is benign, malignant, negative, or other based on a probability of the ROI to be a lesion, or a determination as to subcategories that the ROI falls within based on a probability of the ROI to be a lesion.

According to another exemplary embodiment, the apparatus 200 may assign weights to diagnostic results for collected frames according to one or more standards, and diagnose a reference frame based on the diagnostic results assigned with the weights. For example, the apparatus 200 may diagnose a reference frame based on diagnostic results for collected frames by assigning a weight to a category to which the largest number of diagnostic results belong. There may be various method for assigning a weight, and a weight may be assigned to each characteristic or each category. In addition, the apparatus 200 may assign a weight to a frame collected at a point in time close to the time of determining the reference frame. Further, a lesion's features, confidence, accuracy, and any other factor may be considered. There may be various standards for assigning a weight, so they may be contemplated as falling within the scope of the exemplary embodiments.

If diagnostic results for a plurality of collected frames are used for diagnosis of a reference frame, a more accurate and objective diagnostic result for a reference frame may be obtained, compared to when diagnosing only the reference frame. For example, if more frames are collected, more diagnostic results to be classified as a category, which is considered significant when statistical information is calculated, may be obtained, thereby reducing diagnosis errors.

In addition, if the diagnostic results for selected frames are classified into characteristics, such as shape, orientation, margin, lesion boundary, echo pattern, posterior acoustic features, surrounding tissue, and the like, and then used for diagnosis of the reference frame, a more accurate diagnostic result for the reference frame may be obtained, compared to diagnosing only the reference frame.

The methods and/or operations described above may be recorded, stored, or fixed in one or more computer-readable storage media that includes program instructions to be implemented by a computer to cause a processor to execute or perform the program instructions. The media may also include, alone or in combination with the program instructions, data files, data structures, and the like. Examples of computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The described hardware devices may be configured to act as one or more software modules in order to perform the operations and methods described above, or vice versa. In addition, a computer-readable storage medium may be distributed among computer systems connected through a network and computer-readable codes or program instructions may be stored and executed in a decentralized manner.

A number of examples have been described above. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for diagnosis of a medical image, comprising:
   a storage having a predetermined size, the storage being configured to store sample frames sampled from among received frames which are received from a medical imaging device; and
   at least one processor configured to:
      once a reference frame including a region of interest (ROI) is determined, select one or more sample frames from among the sample frames stored in the storage, wherein the selected one or more sample frames include an ROI corresponding to the ROI included in the reference frame;
      diagnose each of the selected one or more sample frames; and
      provide a diagnosis for the reference frame based on one or more diagnostic results of the selected one or more sample frames,
   wherein the at least one processor is further configured to select the sample frames, to be stored in the storage, from among the received frames based on detecting a change in a scanning characteristic of a probe, and store the selected sample frames in the storage, and
   wherein the scanning characteristic relates to an orientation angle of the probe with respect to a subject of examination.

2. The apparatus of claim 1, wherein the storage samples the received frames according to at least one from among a predetermined selection standard, a variable selection standard for a variable situation, or an empirical selection standard.

3. The apparatus of claim 1, wherein the storage is configured to store sample frames that are selected by an input of a user.

4. The apparatus of claim 1, wherein the at least one processor is further configured to select a most diagnostic result from among the one or more diagnostic results, and provide the selected diagnostic result as the diagnosis for the reference frame.

5. The apparatus of claim 1, wherein the at least one processor is further configured to classify the one or more diagnostic results into a plurality of categories and calculate statistical data for each category of the plurality of categories.

6. The apparatus of claim 1, wherein the at least one processor is further configured to assign weights to the one or more diagnostic results according to one or more standards, and provide the diagnosis for the reference frame based on the one or more diagnostic results assigned with the weights.

7. The apparatus of claim 1, further comprising:
a display configured to display at least one from among the diagnosis for the reference frame and the one or more diagnostic results associated with the one or more collected sample frames using statistical information relating to frequency distribution.

8. The apparatus of claim 1 wherein the scanning characteristic relates to at least one from among a position of the probe, an angle of the probe, or a speed of the probe.

9. The apparatus of claim 1, wherein the change in the scanning characteristic is determined by comparing the scanning characteristic to a threshold scanning characteristic.

10. An apparatus for diagnosis of a medical image, comprising:
at least one processor configured to:
once a reference frame including a region of interest (ROI) is determined, select one or more frames to be used for diagnosis of the reference frame by sampling a plurality of frames which are received from a medical imaging device, wherein the selected one or more frames include an ROI corresponding to the ROI included in the reference frame;
diagnose each of the selected one or more frames; and
provide a diagnosis for the reference frame based on one or more diagnostic results of the selected one or more frames,
wherein the at least one processor is further configured to select the one or more frames by sampling the plurality of frames based on detecting a change in a scanning characteristic of a probe, and store the selected one or more frames in a storage, and
wherein the scanning characteristic relates to an orientation angle of the probe with respect to a subject of examination.

11. The apparatus of claim 10, wherein the at least one processor is further configured to sample the frames according to at least one from among a predetermined selection standard, a variable selection standard for a variable situation, an empirical selection standard.

12. The apparatus of claim 11, wherein the predetermined selection standard comprises at least one from among a predetermined period of time, size of a storage, a total number of frames to be sampled, and accuracy of diagnosis.

13. The apparatus of claim 11, wherein the variable selection standard comprises comparing at least one from among a change with respect to a probe or a change with respect to a frame.

14. The apparatus of claim 11, wherein the empirical selection standard is based on an indicator associated with learning or inferring an intention of a user.

15. The apparatus of claim 10, wherein the at least one processor is further configured to select a most diagnostic result from among the one or more diagnostic results and provide the selected diagnostic result as the diagnosis for the reference frame.

16. The apparatus of claim 10, wherein the at least one processor is further configured to classify the one or more diagnostic results into a plurality of categories, calculate statistical data for each category of the plurality of categories, and provide the diagnosis for the reference frame using the calculated statistical data.

17. The apparatus of claim 10, wherein the at least one processor is further configured to assign weights to the diagnostic results of the selected one or more frames according to one or more standards, and provide the diagnosis for the reference frame based on the one or more diagnostic results assigned with the weights.

18. A method for diagnosis of a medical image, comprising:
sampling frames from among received frames, the received frames being received from a medical imaging device;
storing the sampled frames within a storage having a predetermined size;
once a reference frame including a region of interest (ROI) is determined, selecting one or more sample frames to be used for diagnosis of the reference frame, wherein the selected sample frames include an ROI corresponding to the ROI included in the reference frame;
diagnosing each of the selected one or more sample frames; and
providing a diagnosis for the reference frame based on one or more diagnostic results of the selected one or more sample frames,
wherein sampling the frames from among received frames comprises:
selecting the frames, to be stored in the storage, from among the received frames based on a detected change in a scanning characteristic of a probe, and
wherein the scanning characteristic relates to an orientation angle of the probe with respect to a subject of examination.

19. The method of claim 18, wherein the received frames are sampled according to at least one from among a predetermined selection standard, a variable selection standard for a variable situation, an empirical selection standard.

20. A method of diagnosing a medical image, comprising:
once a reference frame including a region of interest (ROI) is determined,
selecting one or more frames to be used for diagnosis of the reference frame by sampling a plurality of frames which are received from a medical imaging device, wherein the selected one or more frames include an ROI corresponding to the ROI included in the reference frame;
diagnose each of the selected one or more frames; and providing a diagnosis for the reference frame based on one or more diagnostic results of the selected one or more frames, wherein selecting the one or more frames comprises:
 selecting the one or more frames by sampling the plurality of frames based on a detected change in a scanning characteristic of a probe; and
 storing the selected one or more frames in a storage, wherein the scanning characteristic relates to an orientation angle of the probe with respect to a subject of examination.

\* \* \* \* \*